United States Patent
Rae et al.

(10) Patent No.: US 6,288,085 B1
(45) Date of Patent: Sep. 11, 2001

(54) PIPERIDINE DERIVATIVES FOR TREATING PSYCHOSES

(75) Inventors: Duncan Robertson Rae, Lanark; Samuel George Gibson, Motherwell, both of (GB)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/308,035

(22) PCT Filed: Nov. 12, 1997

(86) PCT No.: PCT/EP97/06321

§ 371 Date: Jun. 17, 1999

§ 102(e) Date: Jun. 17, 1999

(87) PCT Pub. No.: WO98/21206

PCT Pub. Date: May 22, 1998

(30) Foreign Application Priority Data

Nov. 14, 1996 (EP) .................................. 96203175

(51) Int. Cl.⁷ .................... A61K 31/445; C07D 409/06
(52) U.S. Cl. .................... 514/326; 514/319; 514/320; 514/324; 546/196; 546/202; 546/205; 546/213; 546/214
(58) Field of Search .................... 514/319, 320, 514/324, 326; 546/196, 202, 205, 213, 214

(56) References Cited

U.S. PATENT DOCUMENTS

| | | | |
|---|---|---|---|
| 2,739,968 | 3/1956 | Sperber et al. | 546/194 |
| 3,687,956 * | 8/1972 | Zivkovic | 546/239 |
| 4,797,489 | 1/1989 | Abou-Gharbia et al. | 544/331 |
| 5,683,998 * | 11/1997 | Shibayama et al. | 514/218 |

FOREIGN PATENT DOCUMENTS

| | | |
|---|---|---|
| 587845 | 5/1977 | (CH) . |
| 2745742 | 4/1978 | (DE) . |
| 0110435 | 6/1984 | (EP) . |
| 0378255 | 7/1990 | (EP) . |
| 0465254 | 1/1992 | (EP) . |
| 1320481 * | 6/1973 | (GB) . |

OTHER PUBLICATIONS

Coupet et al. Brain histamine H1 and . . . CA 95:580800, 1981.*
Kilbourn et al. "Thiphenes as phenyl bio–isosteres . . . " CA 112:73006, 1989.*

* cited by examiner

Primary Examiner—Ceila Chang
(74) Attorney, Agent, or Firm—Michael G. Sullivan

(57) ABSTRACT

The present invention relates to certain novel piperidine derivatives, to processes for their preparation, to pharmaceutical formulations containing them and to their use in medical therapy, particularly in the treatment of psychotic disorders.

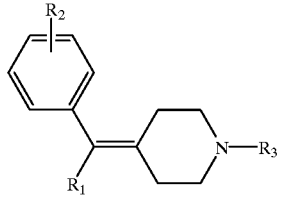

(I)

9 Claims, No Drawings

PIPERIDINE DERIVATIVES FOR TREATING PSYCHOSES

This application is a 371 of PCT/EP97/06321 filed Nov. 12, 1997.

The present invention relates to certain novel piperidine derivatives, to processes for their preparation, to pharmaceutical formulations containing them and to their use in medical therapy, particularly in the treatment of psychotic disorders.

FIELD OF THE INVENTION

U.S. Pat. No. 2,739,968 describes substituted piperidine derivatives having antihistaminic, antispasmodic, antiacetylcholine and analgesic activity.

BACKGROUND OF THE INVENTION

GB patent No.1 320 481 discloses certain gem-diarylethylene derivatives having anti-histamine activity.

Effective antipsychotic (neuroleptic) agents include tricyclic phenothiazines, thioxanthenes and dibenzazepines as well as benzamides and butyrophenones. These compounds block dopamine D2 receptors and inactivate dopamine transmission. As a result of this, these compounds induce characteristic neurological side effects in man such as extrapyramidal side effects e.g. dystonia and dyskinesia (R. J. Baldessarini, 1996, Goodman and Gilman's The Pharmacological Basis of Therapeutics 9th ed., eds J. G. Hardman et. al.). In animal tests such side effects manifest themselves as catalepsy. It would be advantageous therefore to provide a series of antipsychotic agents which do not have these debilitating side effects.

SUMMARY OF THE INVENTION

The present invention provides certain piperidine derivatives which have potent antipsychotic activity but exhibit no cataleptic effects, and thus would not induce extrapyramidal side effects in the therapeutic dose range.

DETAILED DESCRIPTION OF THE INVENTION

Accordingly, the present invention provides the compounds of formula (I)

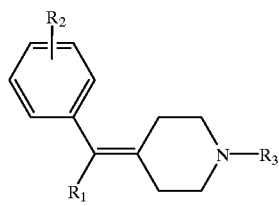

(I)

wherein $R_1$ is benzothienyl, benzofuranyl or naphthyl (where the benzothienyl, benzofuranyl or naphthyl moiety may be optionally substituted by one or more substituents selected from halogen, $C_{1-6}$alkoxy, $C_{1-6}$alkyl, $C_{3-6}$cycloalkyl and $C_{1-6}$-alkenyl), substituted-thienyl or substituted-furanyl (where the thienyl or furanyl moiety is substituted by one or more substituents selected from halogen, $C_{1-6}$alkyl, $C_{3-6}$cydoalkyl and $C_{1-6}$alkenyl); $R_2$ is halogen and $R_3$ is $C_{1-6}$alkyl or $C_{3-6}$cycloalkylmethyl; or a pharmaceutically acceptable salt or solvate thereof.

The present invention includes the piperidine derivatives of formula (I) wherein $R_1$ is benzothienyl, benzofuranyl, naphthyl (where the benzothienyl, benzofuranyl or naphthyl moiety may be optionally substituted by one or more substituents selected from halogen or $C_{1-6}$alkoxy), substituted-thienyl or substituted-furanyl (where the thienyl or furanyl moiety is substituted by one or more substituents selected from halogen or $C_{1-6}$alkyl; $R_2$ is halogen and $R_3$ is $C_{1-6}$alkyl.

More preferred are the piperidine derivatives according to formula I wherein $R_1$ is benzothienyl, benzofuranyl (where the benzothienyl or benzofuranyl moiety may be optionally substituted by one or more substituents selected from halogen or $C_{1-6}$-alkoxy), substituted-thienyl or substitutefuranyl (where the thienyl or furanyl moiety is substituted by one or more substituents selected from halogen or $C_{1-6}$alkyl; $R_2$ is halogen and $R_3$ is $C_{1-6}$alkyl.

Examples of compounds of formula (I) above include the piperidine derivatives described in examples 1 to 7.

As used herein the term alkyl means a straight or branched chain alkyl group. Such alkyl groups include methyl, ethyl, i-propyl, n-propyl, n-butyl, s-butyl, t-butyl, n-pentyl, isopentyl, neopentyl, n-hexyl, isohexyl and neohexyl. Such alkyl groups are preferably $C_{1-4}$alkyl. Reference to cycloalkyl includes cyclopropyl and cyclopentyl. $C_{3-6}$cycloalkylmethyl includes cyclopropylmethyl and cyclopentylmethyl.

References to alkenyl groups include groups which may be in the E- or Z- form or a mixture thereof and which when they contain at least three carbon atoms, may be branched. Such alkenyl groups are preferably $C_{1-4}$alkenyl. Examples of particular alkenyl groups include vinyl, allyl, isopropenyl, butenyl, isobutenyl, pentenyl, isopentenyl, hexenyl, isohexenyl and neohexenyl.

The term alkoxy has the meaning as understood by the person skilled in the art and includes straight and branched chains. Examples of alkoxy groups include methoxy and ethoxy. Preferred alkoxy groups include $C_{1-4}$alkoxy.

The term halogen includes chloro, bromo, fluoro and iodo.

The benzothienyl, benzofuranyl, naphthyl, substituted-thienyl and substituted-furanyl moieties include 2- and 3-benzothienyl, 2- and 3-benzofuranyl, 2- and 3-naphthyl, substituted-2-thienyl, substituted-3-thienyl, substituted-2-furanyl and substituted-3-furanyl groups. The benzothienyl, benzofuranyl, naphthyl, thienyl and furanyl ring substituent(s) may be in any one of the available positions. Specific examples of ring substituents include fluoro, chloro and methoxy.

A preferred example of $R_1$ is a substituted-thienyl, most preferably a substituted-2-thienyl, where the thienyl moiety is substituted by one or more substituents selected from halogen, preferably a chloro atom and $C_{1-6}$alkyl, preferably methyl or ethyl, most preferable methyl.

A preferred example of $R_2$ is fluoro, most preferably 4-fluoro. $R_3$ is preferably methyl.

Preferred compounds according to the present invention include compounds of formula (I) wherein $R_1$ is a substituted-thienyl where the thienyl moiety is substituted by one or more substituents selected from halogen and $C_{1-6}$alkyl; $R_2$ is halogen; and $R_3$ is $C_{1-6}$alkyl; or a pharmaceutically acceptable salt or solvate thereof.

Further preferred compounds of formula (I) include those wherein $R_1$ is a substituted-2-thienyl where the thienyl moiety is substituted by one or more sub-stituents selected from chloro and methyl, most preferably 4-chloro and 4-methyl; $R_2$ is fluoro, most preferably 4-fluoro and $R_3$ is methyl; or a pharmaceutically acceptable salt or solvate thereof.

Particularly preferred compounds according to the invention, which have been found to be useful in the treatment of psychotic disorders, are:

1-methyl-4-[(4-chloro-2-thienyl)-(4-fluorophenyl)]
methylene-piperidine and
1-methyl-4-[(4-methyl-2-thienyl)-(4-fluorophenyl)]
methylenepiperidine;
or a pharmaceutically accptable salt or solvate thereof.

For therapeutic use, salts of the compounds of formula (I) are those wherein the counterion is pharmaceutically acceptable. However, salts of acids which are non-pharmaceutically acceptable may also find use, for example, in the preparation or purification of a pharmaceutically acceptable compound. All salts, whether pharmaceutically acceptable or not are included within the ambit of the present invention.

Examples of pharmaceutically acceptable acid addition salts include those derived from mineral acids such as hydrochloric, hydrobromic, hydroiodic, phosphoric, metaphosphoric, nitric and sulphuric acids, and organic acids, such as tartaric, acetic, trifluoroacetic, citric, malic, lactic, maleic, malonic, fumaric, benzoic, ascorbic, propionic, glycolic, gluconic, succinic and methanesulphonic and arylsulphonic, for example benzene or p-toluenesulphonic acids.

Preferred salts according to the invention include hydrochloric, maleic, succinic and fumaric acid addition salts.

Solvates according to the invention include hydrates.

In a further aspect of the invention there are provided the compounds of formula (I) and their pharmaceutically acceptable salts and solvates for use in therapy, more particularly in the treatment or prophylaxis of psychotic disorders such as schizophrenia, mania, hyperactivity, substance abuse, emesis and schizophreniaform disorders.

The present invention further includes a method for the treatment of an animal, for example, a mammal including a human, suffering from or liable to suffer from a psychotic disorder, induding any of the aforementioned disorders, which comprises administering an effective amount of a compound of formula (I) or a pharmaceutically acceptable salt or solvate thereof.

In yet a further aspect, the present invention provides the use of a compound of formula (I) or a pharmaceutically acceptable salt or solvate thereof in the manufacture of a medicament for the treatment or prophylaxis of any of the aforementioned disorders.

The amount of a compound of formula (I) or a pharmaceutically acceptable salt or solvate, also referred to herein as the active ingredient, which is required to achieve a therapeutic effect will, of course, vary with the particular compound, the route of administration, the age and condition of the recipient, and the particular disorder or disease being treated.

A suitable daily dose for any of the above mentioned disorders will be in the range of 0.001 to 25 mg per kilogram body weight of the recipient (e.g. a human) per day, preferably in the range of 0.1 to 10 mg per kilogram body weight per day and most preferably in the range 0.25 to 5 mg per kilogram body weight per day. The desired dose may be presented as one, two, three, four, five or more sub-doses administered at appropriate intervals throughout the day.

While it is possible for the active ingredient to be administered alone, it is preferable to present it as a pharmaceutical formulation. Accordingly, the present invention further provides a pharmaceutical formulation comprising a compound of formula (I) or a pharmaceutically acceptable salt or solvate thereof, together with a pharmaceutically acceptable carrier thereof and optionally other therapeutic agents. The carrier must be "acceptable" in the sense of being compatible with the other ingredients of the formulation and not deleterious to the recipients thereof.

Formulations include those suitable for oral, rectal, nasal, topical (including transdermal, buccal and sublingual), vaginal or parenteral (including subcutaneous, intramuscular, intravenous, intradermal and intravitreal) administration. The formulations may be prepared by any methods well known in the art of pharmacy, for example, using methods such as those described in Gennaro et al., Remington's Pharmaceutical Sciences (18th ed., Mack Publishing Company, 1990, see especially Part 8: Pharmaceutical Preparations and their Manufacture). Such methods include the step of bringing into association the active ingredient with the carrier which constitutes one or more accessory ingredients. Such accessory ingredients include those conventional in the art, such as, fillers, binders, diluents, disintegrants, lubricants, colorants, flavoring agents and wetting agents.

Formulations suitable for oral administration may be presented as discrete units such as pills, tablets or capsules each containing a predetermined amount of active ingredient; as a powder or granules; as a solution or suspension. The active ingredient may also be presented as a bolus or paste, or may be contained within liposomes.

Formulations for rectal administration may be presented as a suppository or enema. For parenteral administration, suitable formulations include aqueous and non-aqueous sterile injection. The formulations may be presented in unit-dose or multi-dose containers, for example, sealed vials and ampoules, and may be stored in a freeze dried (lyophilised) condition requiring only the addition of the sterile liquid carrier, for example, water prior to use.

Formulations suitable for administration by nasal inhalation include fine dusts or mists which may be generated by means of metered dose pressurised aerosols, nebulisers or insufflators.

The compounds of formula (I) may be produced by various methods known in the art of organic chemistry chemistry in general. Starting materials are either known and readily available from chemical sources or may themselves be produced by conventional techniques. For example, the compounds may be synthesised using methods described in "The Chemistry of Heterocyclic Compounds", vol 44, "Thiophene and its derivatives", parts 1–5, Ed S. Gronowitz J. Wiley and Sons and A. R. Katritsky and C. W. Rees, "Comprehensive Heterocyclic Chemistry", Part 4 Ed C. W. Bird and G. H.Cheesman, Pergamon Press.

The present invention further includes the following processes for the preparation of compounds of formula (I).

In the following description the symbols $R_1$, $R_2$ and $R_3$ have the meanings ascribed to them in formula (I) unless otherwise stated.

Compounds of formula (I) may be prepared by reacting a compound of formula (II)

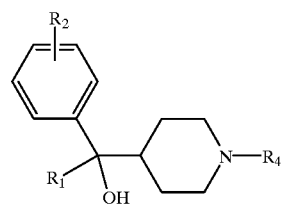

(II)

wherein $R_4$ is a group $R_3$ as defined in relation to formula (I), with a suitable dehydrating agent, for example, a mineral acid such as hydrochloric acid or by using phosphorus oxychloride. The reaction may be conveniently carried out using standard conditions for dehydration of an alcohol. For example, by use of phosphorus oxychloride in the presence of a suitable solvent such as pyridine at a temperature in the range of 80 to 120° C.

Other methods well known to a skilled person or readily available from the chemical literature may be used for the dehydration, including sulphuric acid, 4-methylbenzenesulphonic acid, trifluoroacetic acid, methanesulphonic acid, trifluoromethanesulphonic acid, thionyl chloride, or by use of Martin sulphurane dehydrating agent, employing, where necessary the appropriate solvent.

In the alternative, compounds of formula (II) supra wherein $R_4$ is a nitrogen protecting group, for example trityl, may using methods well known to a skilled person or readily available from the chemical literature, be either simultaneously or sequentially dehydrated and deprotected to form a compound of formula (III)

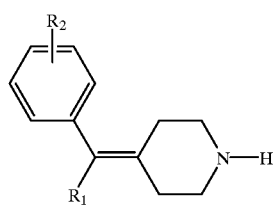

(III)

Alkylation of the compounds of formula (III) results in the preparation of a compound according to the present invention.

Suitable alkylating agents include alkyl halides such as alkyl iodides, for example, ethyliodide or n-butylbromide. The reaction may conveniently be carried out in the presence of a base, for example, potassium acetate or triethylamine, in a suitable solvent such as acetone at a temperature in the range of 0 to 50° C. or in an inert solvent such as toluene or xylene at a temperature in the range of 80–120° C.

Compounds of formula (III) may in the alternative be acylated with an appropriate acid chloride in the presence of pyridine followed by reduction to a compound of formula (I) using methods well known in the art for the reduction of amides. For example, reduction with lithium aluminium hydride.

Where necessary or desired, following one of the above processes, any one or more of the following further steps in any order may be performed:

(i) converting a pharmaceutically acceptable salt or solvate of a compound of formula (I) into a compound of formula (I).
(ii) converting a pharmaceutically acceptable salt or solvate of a compound of formula (I) into another pharmaceutically acceptable salt or solvate of formula (I).
(iii) converting a compound of formula (I) into a pharmaceutically acceptable salt or solvate of a compound of formula (I)

Compounds of formula (II) wherein $R_4$ is a group $R_3$ as defined in relation to formula (I) above, may be prepared by addition of a suitable organometallic reagent, such as a Grignard reagent derived, for example, from 1-methyl-4-chloropiperidine to a compound of formula (IV)

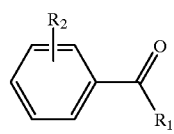

(IV)

The reaction is typically carried out in the presence of an apolar aprotic solvent such as ether or tetrahydrofuran, at a temperature of −30 to 67° C.

Compounds of formula (II) may also be prepared by treating compounds of formula (V)

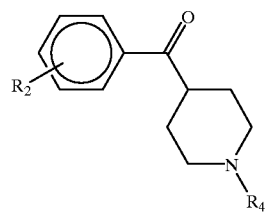

(V)

wherein $R_4$ is a group $R_3$ as defined in relation to formula (I) or a nitrogen protecting group, with an appropriate organometallic reagent, such as a Grignard, or a lithium reagent derived from $R_1$—L in which L is an appropriate halogen, such as bromo or chloro, or a lithio reagent derived from an activated aryl hydrogen atom. The reaction is typically carried out in the presence of an apolar aprotic solvent such as ether or tetrahydrofuran at a temperature in the range of −60 to 67° C.

Alternatively, compounds of formula (II) may be prepared by treating compounds of formula (VI)

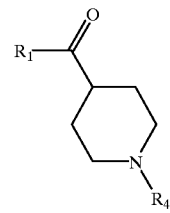

(VI)

wherein $R_4$ is a group $R_3$ as defined in relation to formula (I) or a nitrogen protecting group, with an appropriate organometallic reagent, such as a Grignard, or a lithium reagent derived from the appropriate halo substituted benzene. For example, compounds of formula (II) wherein the phenyl group is subsituted with a halo atom may conveniently be prepared by treating a compound of formula (VI) with the appropriate halo substituted phenyl magnesium halide using standard reaction conditions.

Compounds of formula (IV) may be prepared by methods known in the chemical literature. For example, compounds wherein $R_1$ is 4-chloro- or 2,3-dichloro-thienyl may be prepared, for example, as described in example 1 by chlorination of the appropriately substituted halobenzoylthiophene. These compounds are commerdialy available or are prepared using methods known in the art, for example, by Friedel-Crafts benzoylation of the thiophene or other groups represented by $R_1$.

In an alternative method, compounds of formula (IV) may be prepared by Friedel-Crafts acylation or benzoylation of 3-chloro-2-bromo-thiophene in the presence of a catalyst such as ferric chloride or aluminium chloride in an apolar solvent such as dichloromethane at a temperature in the range of 10–25° C. Reductive de-bromination of the initially formed product gives the required compounds. Such reduction may be carried out by catalytic hydrogenation using a suitable catalyst such as palladium on charcoal in a suitable solvent such as ethanol or acetic acid at a temperature in the range of 15–25° C. and at a pressure of between 1 and 50 psi, or by use of activated zinc in the above mentioned solvents at a temperature in the range of 20–65° C.

Compounds of formulae (V) and (VI) may, for example, be prepared by the addition of the appropriate Grignard reagent to ethyl N-methyl or N-trityl isonipecotate. The latter compounds are commercially available or may be prepared from commercially available compounds using methods known in the art.

Alternatively, compounds of formula (V) wherein $R_4$ is methyl or hydrogen and $R_2$ is 4-fluoro may be prepared by methods described in *J. Med.Chem.*, 1970, 13, 1 Compounds of formula (V) wherein $R_4$ is trityl may be prepared from compounds of formula (V) wherein $R_4$ is hydrogen, for example by reaction with trityl bromide using the method described in Example 4 infra.

Compounds of formula (III) supra may be prepared by converting a compound of formula (I) wherein $R_3$ is methyl to its urethare derivative. The reaction may conveniently be carried out with a chloroformate, such as ethyl-, benzyl- or trichloroethyl-chloroformate (see Baldwin, S. W.; Jeffs, P. W.; Natarajan, S., Gross, P. M., *Synthetic. Commun*, 1977, 7, 79; Kraiss, G., and Nader, K. Tetrahedron Letters, 1971, 57). Hydrolysis of these urethane derivatives, for example, with a mineral acid, such as hydrochloric acid or by treatment in appropriate circumstances with zinc gives the compound of formula (III).

Salts according to the present invention may be prepared by treating a compound of formula (I) with an appropriate base, for example an alkali metal, alkaline earth metal or ammonium hydroxide, or an appropriate organic or inorganic acid, such as hydrochloric, fumaric or maleic acid.

The present invention further includes all novel intermediates hereinbefore described and in particular compounds of formula (II). Specific intermediates according to the present invention include:

α-(4-fluorophenyl)-α-(-4-chloro-2-thienyl)-1-methyl-4-piperidinemethanol;

α-(4-fluorophenyl)-α-(-4-methyl-2-thienyl)-1-methyl-4-piperidinemethanol;

α-(4-fluorophenyl)-α-(4,5-dichloro-2-thienyl)-1-methyl-4-piperidinemethanol;

α-(4-fluorophenyl)-α-(5-ethyl-2-thienyl)-1-methyl-4-piperidinemethanol;

α-(4-fluorophenyl)-α-(4-ethyl-2-thienyl) 1-methyl-4-piperidinemethanol;

α-(4-fluorophenyl)-α-(2-benzothienyl)-1-methyl-4-piperidinemethanol;

α-(4-fluorophenyl)-α-(5-fluoro-2-benzothienyl)-1-methyl-4-piperidinemethanol;

α-(4-fluorophenyl)-α-(6-methoxy-2-benzothienyl)-1-methyl-4-piperidinemethanol;

α-(4-fluorophenyl)-α-(2-benzofuranyl)-1-methyl-4-piperidinemethanol;

α-(4-fluorophenyl)-α-(4,5-dimethyl-2-furanyl)-1-methyl-piperidinemethanol; and

α-(4-fluorophenyl)-α-(4-methyl-2-thienyl)-1-triphenylmethyl-4-piperidinemethanol.

The following examples are intended for illustration only and are not intended to limit the scope of the invention in any way.

EXAMPLE 1

1. Preparation of 2-chloro-4-(4-fluorobenzoyl)-thiophene

Crushed aluminium chloride (24.3 g) was added to a stirred solution of 2-(4-fluorobenzoyl)-thiophene (15.0 g) in dry dichloromethane (150 ml) at ~5° C. and after 1 h a solution of chlorine [5.16 g in carbon tetrachloride (26.3 ml)] was added dropwise, maintaining the temperature at ~5° C. When the addition was complete, the temperature was allowed to rise to ~12° C., over 1.5 h, and the reaction mixture was stirred at this temperature for 1 h The solution was recooled to ~5° C., a further quantity of chlorine (1.3 g) in carbon tetrachloride (6.8 ml) was added and the solution was stirred at this temperature for a further 1 h then allowed to stand overnight at ~20° C. The solution was again re-cooled to 5° C., a further amount of chlorine (2.6 g) in carbon tetrachloride (13 ml) was added, the temperature was raised to ~20° C. and the mixture was stirred for 2 h. The mixture was cooled in an icebath, water (200 ml) was added followed by ether (400 ml) and the layers were separated. The ether layer was washed neutral with water, dried over $Na_2SO_4$ and evaporated to give a brown gum (18.9 g) which was crystallised from etherihexane to give 2-chloro-4-(4-fluorobenzoyl)-thiophene, (10.3 g), 77.6% (GLC).

2. Preparation of 2,3-dichloro-4-(4-fluorobenzoyl)-thiophene

The mother liquor from the previous example was chromatographed on silica. Elution with toluene/hexane (4:1) gave a fraction which was evaporated and the residue was crystallised from etherlhexane to give the titled compound, (1.9 g), m.p. 104–105° C.

EXAMPLE 2

A: 1-Methyl-4-[(4-chloro-2-thienyl)-(4-fluorophenyl)]methylene-piperidine (fumarate salt)

4-Chloro-1-methylpiperidine.HCl (18.7 g) was basified with aq. ammonium hydroxide and the solution was extracted with ether and the extract was washed with brine, dried ($Na_2SO_4$) and evaporated to give 4-chloro-1-methylpiperidine (14.7 g) as an almost colourless oil.

A crystal of iodine was added to a stirred suspension of magnesium turnings (2.32 g) in redistilled tetrahydrofuran (THF) (10.0 g), followed by ethyl bromide (0.16 ml) and, after the iodine colour had disappeared (~5 min), a solution of the above 4-chloro-1-methylpiperidine (14.4 g) in THF (96 ml) was added dropwise over ~30 min; a small amount of heating was applied so as to maintain a gentle reflux. After the addition was complete the mixture was boiled under reflux for a further 1.5 h then cooled to ~0° C. A solution of 2-chloro-4-(4-fluorobenzoyl)thiophene (10.3 g; example 1) in THF (25 ml) was added dropwise over 40 min to the solution keeping the temperature below 10° C. and the mixture was boiled under reflux for 2.5 h.

A saturated solution of ammonium chloride (100 ml) was added to the cooled mixture, followed by ether (500 ml), the insolubles were filtered off through dicalite and the layers were separated. The ether layer was washed with water, dried ($Na_2SO_4$) and evaporated to yield a brown gum (18.2 g)

A mixture of hydrochloric acid (5 N; 60 ml) and hydrochloric acid (2N; 60 ml) was added to the above brown gum (10.8 g) and the stirred mixture was boiled under reflux for 0.75 h. When total solution occurred the reaction mixture was cooled to ~5° C. and basified with aq. ammonium hydroxide. The product was extracted with dichloromethane, the extract was washed with water, dried (Na$_2$SO$_4$) and evaporated to give a brown gum (8.2 g) which was chromatographed on silica. Elution with dichloromethanelmethanol (gradient elution 1–10% methanol gave a fraction which was evaporated to give α-(4-fuorophenyl)-α-(4-chloro-2-thienyl)-1-methyl-4-piperidinemethanol (1.07 g) containing some overchlorinated impurity. Zinc dust (1.56 g) was added to a suspension of the crude product (0.78 g) in sodium hydroxide solution (4N; 7.8 ml) and the mixture boiled under reflux for 2.5 h. The mixture was cooled, water (15 ml) was added and the product was extracted into dichloramethane (30 ml. The extract was washed with water (3×30 ml), dried (Na$_2$SO$_4$) and evaporated to give a brown gum (0.75 g). This crude material was dissolved in methanol, a solution of fumaric acid in methanol was added and the solution was evaporated to a low volume. Ether was added and the resultant crystals were collected to give the pure title compound as a pale solid (0.71 g); m.p. 209–210° C.

B: The succinate salt of 1-methyl-4-[(4-chloro-2-thienyl)-(4-fluorophenyl)]-methylene-piperidine methyl; was similarly prepared; m.p. 161–169° C.

C: In a similar manner, but without the need to remove overchlorinated material, 2,3-dichloro-4-(4-fluorobenzoyl)-thiophene was converted to 1-methyl-4-[(4,5-dichloro-2-thienyl)-(4-fluorophenyl)]methylenepiperidine.fumarate; m.p. 220° C.

D: Methyl-4-[(4-chloro-2-thienyl)-(4-fluorophenyl)]methylene-piperidine (alternative method of preparation)

i: 2-bromo-3-chloro-thiophene

A solution of N-bromosuccinimide (221.7 g) in dimethylformamide (550 ml) was added dropwise over 75 min to a stirred solution of 3-chlorothiophene (143.4 g) and perchloric acid (70%, 5.8 ml) cooled in an ice-water bath at 15° C. The reaction temperature gradually rose to 40° C. over 30 min and then was cooled to 11° C. Cooling was removed and the reaction was stirred for a further 2 h. The reaction was poured into water and exacted with methyltertbutyl ether. The organic extract was sequentially washed with water, aq. sodium hydrogen sulphite solution and water, dried (Na$_2$SO$_4$) and evaporated to dryness. The residual oil (246 g) was distilled under vacuum in an oil bath at 80–90° C. to give 2-bromo3-chloro-thiophene as an oil (202 g (97%); b pt 42° C. (1 mm Hg).

ii: 2-bromo-3-chloro-5-(4-fluorobenzoyl)thiophene

Ferric chloride (301.2 g) was added to a stirred solution of 2-bromo-3-chlorothiophene (148.5 g) and 4-fluorobenzoyl chloride (169.7 g) in dichloromethane (2230 ml), cooled to 18° C. in an icetwater bath. The temperature of the reaction mixture rose to 22° C. and was then cooled to 12° C. Cooling was removed and the reaction mixture was stirred for a further 50 min during which time the internal temperature rose to 16° C. The reaction mixture was re-cooled to 10° C., water (700 ml) was added carefully, keeping the internal temperature below 15° C., and the mixture was then stirred for 1 h. The dichloromethane layer was separated and the aq layer was washed with dichloromethane. The combined dichloromethane layer was washed with water and saturated sodium bicarbonate solution. The dichloromethane was separated and the aq. layer filtered through dicalite and extracted with dichloromethane. The extract was washed with water, dried (Na$_2$SO$_4$) and evaporated to dryness to give 2-bromo-3-chloro-5-(4-fluorobenzoyl)-thiophene as a solid (233.3 g).

iii: 4-chloro-2-(4-fluorobenzoyl)thiophene

A slurry of 5% palladium on charcoal (20 g) in ethanol (100 ml) was added under nitrogen gas to a solution of the above 2-bromo3-chloro-5-(4-fluorobenzoyl)-thiophene (299.4 9 ) in ethanol (3.400 ml), containing sodium acetate (77.0 g),and the mixture was hydrogenated for 3 hours at room temperature and pressure (total uptake of hydrogen was 22,994 ml). The reaction mixture was filtered through a dicalite pad and the pad was washed with ethanol (2×200 ml). The filtrate was taken to low volume (approximately 2 l) and added to water (17 l). The precipitate was filtered and while damp it was dissolved in dichloromethane (1 l) which was then reduced in volume to approximately 500 ml. Methanol (500 ml) was added and the remainder of the dichloromethane was removed by distillation. The resultant crystals were filtered and dried to give 4-chloro-2-(4-fluorobenzoyl)thiophene as a white solid (169 g). A second crop (19.2 g) was obtained and recrystallised from dichloromethane/methanol to give more of the purified product (12.9 g). The crops were combined and used in the next stage.

iv: α-(4-fluorophenyl)-α-(4-chloro-2-thienyl)-1-methyl-4-piperidinemethanol

A suspension of magnesium turnings (36.7 g) in tetrahydrofuran (470 ml) was heated to 55° C. under nitrogen gas and an aliquot (20.0 ml) of a solution of N-methyl-4-chloropiperidine (221.6 g) in tetrahydrofuran (1400 ml), followed by 1 crystal of iodine and then ethylbromide (14.0 ml were added. Almost immediately initiation occurred as the temperature rose to 64° C. accompanied by the loss of the iodine coloration and onset of reflux. The rest of the N-methyl 4-chloropiperidine solution (containing 14.0 ml of ethylbromide) was then added over 75 min, maintaining a gentle reflux. Once addition was complete the mixture was stirred at 64° C. for a further 90 min, after which only a few grains of magnesium remained. The solution was cooled in an ice/water bath to 20° C., and was then pumped via positive nitrogen pressure, into a solution of 4-chloro-2-(4-fluorobenzoyl)thiophene (140.0 g) in tetrahydrofuran (1.4 l) which had been precoled to 0° C. in an ice/salt bath, over a period of 60 min, keeping the internal temperature below 8° C. The solution was added, over about 40 min, to a cold (5° C.) saturated solution of ammonium chloride (4.6 l), maintaining the temperature below 15° C. The mixture was extracted with ethyl acetate and the extract was washed with water, dried (Na$_2$ SO$_4$) and evaporated to dryness to give a brown gum (202 g). The gum was crystallised from dichloromethanemethyl tertbutyl ether to give a solid which was filtered and washed with cold methyl tert.butyl ether. The solid was filtered and dried and the product (79.2 g) was recrystallised from dichloromethane/methyl tert.butyl ether to give α-(4-fluorophenyl)-α-(4-chloro-2-thienyl)-1-methyl-4-piperidinemethanol (61.6 g).

V: 1-methyl-4-[(4-chloro-2-thienyl)-(4-fluorophenyl)]methylenepiperidine

The above alcohol (73.8 g) was refluxed in a mixture of 2N hydrochloric acid (440 ml) and 5 N hydrochloric acid (440 ml) for 50 min. The reaction mixture was cooled in an ice/water bath and the resulting white precipitate was filtered and washed with water to give white lustrous crystals. The damp crystals were suspended in a mixture of ethyl acetate (300 ml) and water (300 ml) and while stirring, basified with 4 N sodium hydroxide solution (200 ml). The ethyl acetate layer was separated and the aq. layer was extracted with ethyl acetate. The combined extract was washed with water, dried, (Na$_2$SO$_4$) and evaporated to give 1-methyl-4-[(4-chloro-2-thienyl)-(4-fluorophenyl)]methylenepiper as a brown oil (66.8 g). GLC 98% vi: 1-methyl-4-[(4-chloro-2-thienyl)-(4-fluorophenyl)]methylenepiperidine.succinate The above amine (64.6 g)

was dissolved in methanol (640 ml), succinic acid (24.88 g) was added, the solution was taken to dryness and the residual solid (89.4 g was dissolved in hot ethanol (1.1 l). The solution was reduced in volume (200 ml), cooled in an ice/water bath and the resultant solid was filtered and washed with ethanol (200 ml). The solid was dried under vacuo at 50° C. to give 1-methyl-4-[(4-chloro-2-thienyl)-(4-fluorophenyl)]methylenepiperidine succinate (1;1 salt) (78.2 g) as an off-white solid; m.p. 171° C.

EXAMPLE 3

A: Preparation of 1-methyl-4-[(4-methyl-2-thienyl)-(4-fluoroohenyl)]methylenepiperidine.HCl A solution of 3-methylthiophene (3.5 g) in dry THF (40 ml) was added to a solution of n-butyl lithium in hexane (1.6 N; 20 ml) and the solution was boiled under reflux for 2 h. The solution was cooled to 0° C. and a solution of 1-methyl-4-(4-fluorobenzoyl)piperidine (2.1 g) in dry THF (40 ml) was added over 10 min whilst keeping the temperature at ~0° C. The solution was allowed to warm to room temperature, water (20 ml) was cautiously added and the mixture was extracted with ethyl acetate. The extract was re-extracted with hydrochloric acid (1 N), the aqueous extract was basified with aq. ammonium hydroxide and the product was extracted into ethyl acetate. This extract was washed with water, dried ($Na_2SO_4$) and evaporated to give an oil (2.6 g). A solution of this oil (1.7 g) in pyridine (17 ml) containing phosphorous oxychloride (0.1 ml) was heated at 115–120° C. for 8.5 h. The solution was cooled, water was added and the mixture was basified with aq. ammonium hydroxide and extracted with ethyl acetate. The extract was washed with water, dried ($Na_2SO_4$) and evaporated to give the crude product as the free base which was purified by filtration through silica. Treatment of a solution of this free base with an ethereal solution of hydrogen chloride gave a solid which was crystallised from methanol/ether to give 1-methyl-4-[(4-methyl-2-thienyl)-(4-fluorophenyl)]methylene-piperidine.HCl (1.45 g); m.p. 235° C.

B: The Following Compounds Were Prepared in a Similar Manner

Starting from 2-ethylthiophene; 1-methyl-4-[(5-ethyl-2-thienyl)-(4-fluorophenyl)]-methylenepiperdine.maleate; m.p. 175–176° C.

Starting from 3-ethylthiophene; 1-methyl-4-[(4-ethyl-2-thienyl)-(4-fluorophenyl)]methylenepipendine.maleate; m.p. 76.8° C.

Starting from benzothiophene; 1-methy-4-(2-benzothienyl)-(4-fluorophenyl)]methylenepiperidine.maleate, m.p. 197–214° C.

Starting from 5-fluorobenzothiophene; 1-methyl-4-[(5-fluoro-2-benzothienyl)-(4-fluorophenyl)]methylenepiperidine.maleate, m.p. 152–155° C.

Starting from 6-methoxybenzothiophene; 1-methyl-4-[(6-methoxy-2-benzothienyl)-(4-fluorophenyl)]methylenepiperidine.maleate, m.p. 150–153° C.

Starting from; benzofuran; 1-methyl-4-[(2-benzofuranyl)-(4-fluorophenyl)]methylenepiperidine.maleate, m.p. 196.2° C.

Starting from; 2,3-dimethylfuran; 1-methyl-4-[(4,5-dimethyl-2-furanyl)-(4-fluorophenyl)]methylenepiperidine.maleate, m.p. 197–200° C.

EXAMPLE 4

4-[(4-Fluorophenyl)-2-(4-methylthienyl)methylene] piperidine hydrochloride

To a stirred solution of 4-(1-acetylpiperidinyl) chloride (50 g) in dichloromethane (690 ml), under a nitrogen atmosphere, at −25° C., was sequentially added powdered aluminium chloride (71 g) followed by a solution of 2-bromo-3-methylthiophene (50 g) in dichloromethane (300 ml) over 17 min. After 30 min. water (240 ml) was added dropwise to the reaction whilst allowing the reaction temperature to rise to about +20° C. After stirring for a further 30 min the inorganic components were removed by filtration through a pad of dicalite. The layers were separated , the organic layer was washed twice with water, dried ($Na_2SO_4$) and evaporated under reduced pressure. The crude product (73 g) was purified by chromatography to yield 2-(5-bromo-4-methylthienyl)4-(1-acetylpiperidine)methanone (62.2 g); mp 105–108.5° C. (dec).

A suspension of zinc dust (22 g), sodium iodide (11 g), triphenylphosphine (165 g) and nickel chloride hexahydrate (2.56 g) in deoxygenated methanol (340 ml) (prepared by boiling methanol in a stream of nitrogen for 2 h), was stirred in a nitrogen atmosphere at 60° C. for 15 min. To this mixture was added a solution of the above bromo compound (62.2 g) in deoxygenated methanol (150 ml) and the reaction was boiled under reflux in a nitrogen atmosphere for 22 h. The reaction was cooled and the inorganic components were removed by filtration through a pad of dicalite. The filtrate was evaporated and the residue was dissolved in dichloromethane. The solution was washed with dilute mineral acid, followed by water to neutrality, dried ($Na_2SO_4$) and evaporated to dryness under reduced pressure. The crude product (61.3 g) was purified by flash chromatography and crystallised from dichloromethane/ether to give, in two crops, 2-(4-methylthienyl)4-(1-acetylpiperidine)methanone (41.2 g); mp 120–125° C. A solution of this methanone (41.2 g) in 5N aqueous hydrochloric acid (140 ml) was boiled under reflux for 16 h then evaporated under reduced pressure, azeotroping the remaining water with toluene. Trituration of the residue with diethyl ether gave the crude product (38.8 g) which was isolated by filtration. Recrystallisation from a mixture of methanol and diethyl ether gave 2-(4-ethylthienyl)-4-piperidinemethanone hydrochloride in two crops (29.5 g); mp 217.5–218.5° C. (change in crystal form above 200° C.).

A solution of the above hydrochloride (28 g) in water was basified and a solution of this (24.1 g) in dichloromethane (240 ml) and triethylamine (48 ml) was stirred at 0° C. under a nitrogen atmosphere. Triphenylmethyl chloride (33.7 g) was added in portions, at such a rate to maintain the reaction temperature at 0±2° C. After 30 min the mixture was cautiously diluted with water (240 ml) and extracted into dichioromethane. The extract was washed, dried ($Na_2SO_4$) and evaporated under reduced pressure, partially replacing the dichloromethane with heptane, and allowed to crystallise. The crystals were filtered and washed with a 4:1 mixture of heptane and dichloromethane to yield 2-(4-methylthienyl)-4-(1-triphenylmethylpiperidine)-methanone (46.9 g); mp 219–221° C. (decomp).

Bromoethane (1.5 ml) was added to a stirred suspension of magnesium turnings (6.4 g) in dry diethyl ether (100 ml) containing a crystal of iodine. The exothermic reaction was maintained at 32 to 36° C. throughout whilst a solution of 4-bromofluorobenzene (29 ml) in dry diethyl ether (170 ml) was cautiously added. The resulting mixture was gently boiled under reflux for 30 min then cooled to 0° C. To this mixture was added dropwise, over 15 min., a solution of the above methanone (23.5 g) in dry diethyl ether (280 ml) while maintaining the temperature between 0 and 5° C. The reaction was then allowed to warm to room temperature over 30 min and the product was extracted with ethyl acetate. The extracts were washed with water, dried (Na$_2$SO$_4$) and evaporated under reduced pressure to yield a gum (32.4 g) which was dissolved in a mixture of acetic acid (261 ml) and water (130 ml)) and the solution was boiled under reflux for 18 h. Water (130 ml) was added and the reaction was cooled to <5° C. Solid material (triphenylmethyl alcohol) was filtered off and the filtrate was evaporated under reduced pressure to a low volume. The residue was basified with concentrated ammonium hydroxide solution and the product was extracted into ethyl acetate.The extract was washed with aqueous sodium chloride solution, dried (Na$_2$SO$_4$) and evaporated to dryness under reduced pressure to yield a gummy residue (15.0 g). A solution of hydrogen chloride in methanol was added ti a solution of this material in diethyl ether and the solution was allowed to crystallise to give 4-[(4-fluorophenyl)2-(4-methylthienyl)methylene] piperidine hydrochloride (9.0 g); mp 191–206° C. (decomp).

EXAMPLE 5
1-butyl-4-[(5-chloro-2-thienyl)-(4-fluoronphenyl)] methylene-piperidine.fumarate A stirred solution of 4-[(5-chloro-2-thienyl)-(4-fluorophenyl)]methylene-piperidine (0.69 g), 1-bromobutane (0.48 ml) and triethylamine (1.56 ml) in toluene (20 ml) was boiled under reflux for 24 h. The reaction mixture was allowed to cool, transferred to a separating funnel and washed in with toluene (30 ml) and water (30 ml). The mixture was shaken and the toluene layer was separated, washed with water, dried (Na$_2$SO$_4$) and evaporated to give a viscous oil (0.71 g) which was chromatographed on silica. Elution with dichloromethane:methanol 24:1 gave a fraction which was evaporated to give a viscous oil (0.53 g). This oil (0.48 g) was dissolved in methanol (5 ml), a solution of fumaric acid (0.16 g) in methanol (5 ml) was added and the solution was evaporated to a low volume. Ether was added and the resultant crystals were collected to give the titled compound (0.51 g), m.p. 167–172° C.

EXAMPLE 6

In manner similar to that described in example 5, but using (bromomethyl)cyclopropane as alkylating agent, 1-cyclopropylmethyl-4-[(5-chloro-2-thienyl)-(4-fluorophenyl)]methylene-piperidine.fumarate, m.p. 171–172° C. was prepared.

EXAMPLE 7
4-(4-Fluorophenyl-2-naphthyl)-1-methylpiperidine fumarate

A solution of 2-bromo-naphthalene (3.13 g) in dry tetrahydrofuran 10 ml) was added dropwise to a stirred suspension of magnesium turnings (0.37 g) in dry, re-distilled tetrahydrofuran (10 ml) containing a crystal of iodine under an atmosphere of nitrogen. The reaction was warmed to 55° C., heating being discontinued 3 min after the reaction commenced. Towards the end of the addition the temperature was maintained between 50–55° C. by means of a water bath. After a further 15 min the reaction was cooled to 5° C. when a solution of 4-(4-fluorobenzoyl)-N-methylpiperidine (0.81 g) in dry tetrahydrofuran (4 ml) was added keeping the temperature between 5–10° C. The mixture was warmed up to 50° C. over 1 h then cooled to 5° C. when a solution of aqueous ammonium chloride (15 ml) was added. The product was extracted into diethyl ether, the extract was washed with water, dried (Na$_2$SO$_4$) and evaporated to give a white solid (2.41 g) which was chromatographed on silica. Elution with dichloromethane:methanol (95:5, v/v) gave α-(4-fluorophenyl)-α-( 2-naphthyl)-(1 -methyl)-4 piperidinemethanol which was crystallised from dichloromethane on the addition of ether (0.27 g); m.p. 164–169° C.

A suspension the above alcohol (0.81 g) in 3.5N hydrochloric acid (10 ml) was refluxed for 2.5 h, cooled to 20° C. then basifhed with aq. ammonia (5 ml). The product was extracted into dichloromethane(50 ml), the extract was washed with water, dried (Na$_2$SO$_4$) and evaporated to dryness to give 4-(4-fluorophenyl-2-naphthyl)-1-methylpiperidine as a pale yellow gum (0.81 g). This compound was converted to the fumarate as described above and crystallised from methanol on the addition of ether to give the titled compound (0.89 g), m.p. 214–218° C.

EXAMPLE 8

Apomorphine Climbing Test In Mice

The ability of dopamine receptor antagonists to inhibit the behavioural effects in rodents caused by dopamine agonists such as apomorphine is a well established criterion for predicting the antipsychotic efficacy of these drugs in man (see e.g. W. C. Bowman and M. J. Rand, Textbook of Pharmacology, 2nd ed., 1980, 15, 6). A particularly relevant test in this respect is the apomorphine climbing test (ACT) which measures the ability of a dopamine antagonist to inhibit the climbing behaviour in mice, induced by the subcutaneous or oral administration of apomorphine. Activity in this test, following systemic and oral administration, has been widely used as a predictor of antipsychotic activity i.e. anti-schizophrenic activity (see e.g. J. T Strupczewski et.al., *J. Med. Chem.*, 1995, 38, 1119). Mice treated with apomorphine HCl tend to adopt a vertical position along the wall of a wire mesh cylinder, standing or climbing. This climbing behaviour is considered to be elicited by apomorphine-mediated stimulation of dopamine receptors. Many drugs affect the dimbing behaviour, but dopamine antagonists generally inhibit it in doses not interfering with spontaneous motor activity and/or motor coordination in mice. Test compounds which modulate this climbing behaviour may have anti-psychotic activity.

The various treatments are randomly distributed over the mice. Each experiment consists of 1+n treatment groups: 1 being a control group of 12 mice receiving apomorphine and vehicle subcutaneously or being a control group of 12 mice receiving apomorphine subcutaneously and vehicle orally; n being (usually 4) compound groups of 12 mice receiving apomorphine and test compound subcutaneously or being compound groups of 12 mice receiving apomorphine subcutaneously and test compound orally.

Experiments are performed in 3 runs of 20 mice each. The mice are marked and weighed, test compound or vehicle is administered subcutaneously and the mice are placed in small Macrolon cages of 17×11×13 cm, 5 mice per cage, or test compound or vehicle is administered orally and the mice are placed in Macrolon cages of 29×11×13 cm, 5 mice per cage. After 30 min 0.75 mg/kg apomorphine HCl is administered subcutaneously in mice treated subcutaneously with vehicle or test compound, or 0.75 mg/kg apomorphine HCl is administered subcutaneously in mice treated orally with vehicle or test compound, and the mice are placed individually in a wire mesh cylinder (diameter 12 cm, height 14 cm).

At 10 min after the treatment with apomorphine the climbing behaviour of each mouse is observed and expressed as a score, according to the following grade:

4 paws on the floor score 0

1 or 2 paws holding the wall score 1

3 or 4 paws holding the wall score 2

At 20 min after the treatment with apomorphine the climbing behaviour is observed and scored again. For each treatment group the mean score per mouse is determined. The score of the control group should be at least 1.0; if not, the trial is rejected. The final result per group is expressed as the percentage over the control group.

The results of this test for the present test compounds are denoted in Table I (subcutaneous and oral administration of test compound).

TABLE 1

| EXAMPLE No. | ACT(ED$_{50}$) mg/kg | |
| --- | --- | --- |
| | sc | po |
| 2 | 0.6 | 5 |
| 3 | 1.5 | 8.6 |
| Compound A | 2.8 | 100 |
| Compound B | 22 | |
| Compound C | 22 | |

The compounds of Example 2, 1-methyl-4-[(4-chloro-2-thienyl)-(4-fluorophenyl)]-methylene-piperidine, and Example 3, 1-methyl-4-[(4-methyl-2-thienyl)-(4-fluoropheny)]methylene-piperidine, were compared with compound 1-methyl-4-[(2-thienyl)-(4-fluorophenyl)]methylenepiperidine (Compound A) which falls within the scope of U.S. Pat. No. 2,739,968 and compound 1-methyl-4-(2-thienyl)-phenyl-methylenepiperidine (Compound B) according to U.S. Pat. No. 2,739,968 and 1-methyl-4-[(-5-chloro-2-thienyl)-phenyl]methylenepiperidine (Compound C). The compounds according to the invention showed good activity and in particular good oral activity compared with Compound A.

EXAMPLE 9

Catalepsy in rats: Male Wistar rats (100–125 g, Olac UK) were used for catalepsy experiments. Catalepsy was assessed as described previously (Broekkamp et al, *Naunyn Schmiedeberg's Arch. Pharmacol.* 338, 191 1988). Briefly, rats were tested in 6 different observation trials in which the animals were placed in abnormal postures and scored positively with one point for maintaining the imposed posture for 10s. The imposed postures were; vertical clinging to a grid, upright standing with a high support for the front paws, extension of hindlegs, placement on back, placement of spatula in the mouth and rotation in a wire mesh cylinder.

Theoretically a maximum score of 6 can be reached. Catalepsy was assessed at 60 and 120 minutes after drug administration. The data were evaluated by 2 way ANOVAR followed by a Newman Kools post hoc test and ED$_{50}$ values calculated (Table II).

TABLE II

| COMPOUND No | CATR ED50 mg/kg | CATR score at max dose |
| --- | --- | --- |
| 2 | >50 | 0.2 at 56 mg/kg |
| 3 | >75 | 0.2 at 75 mg/kg |
| chlorpromazine | 4.8 | 5.3 at 14 mg/kg |

Cmpd 2 = 1-methyl-4-[(4-chloro-2-thienyl)-(4-fluorophenyl)]methylene-piperidine
Cmpd 3 = 1-methyl-4-[(4-methyl-2-thienyl)-(4-fluorophenyl)]methylene-piperidine

We claim:

1. A compound of formula (I)

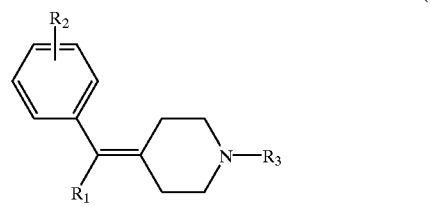

wherein R$_1$ is benzothienyl, benzofuranyl, naphthyl (where the benzothienyl, benzofuranyl or naphthyl moiety may be optionally substituted by one or more substituents selected from halogen, C$_{1-6}$alkoxy, C$_{1-6}$alkyl and C$_{1-6}$alkenyl), substituted-thienyl or substituted-furanyl (where the thienyl or furanyl moiety is substituted by one or more substituents selected from halogen, C$_{1-6}$alkyl, C$_{3-6}$-cycloalkyl and C$_{1-6}$alkenyl); R$_2$ is halogen and R$_3$ is C$_{1-6}$alkyl or C$_{3-6}$cycloalkylmethyl;

or a pharmaceutically acceptable salt or solvate thereof.

2. A compound according to claim 1, wherein R$_1$ is benzothienyl, benzofuranyl, naphthyl (where the benzothienyl, benzofuranyl or naphthyl moiety may be optionally substituted by one or more substituents selected from halogen or C$_{1-6}$-alkoxy), substituted-thienyl or substituted-furanyl (where the thienyl or furanyl moiety is substituted by one or more substituents selected from halogen or C$_{1-6}$alkyl; R$_2$ is halogen and R$_3$ is C$_{1-6}$alkyl;

or a pharmaceutically acceptable salt or solvate thereof.

3. A compound according to claim 1 wherein R$_1$ is thienyl substituted by one or more substituents selected from halogen and C$_{1-6}$alkyl; R$_2$ is halogen and R$_3$ is C$_{1-6}$alkyl;

or a pharmaceutically acceptable salt or solvate thereof.

4. A compound according to claim 1 wherein R$_1$ is 2- or 3-thienyl substituted by one or more substituents selected from chloro and methyl, preferably 4-chloro and 4-methyl; R$_2$ is fluoro; and R$_3$ is methyl;

or a pharmaceutically acceptable salt or solvate thereof.

5. A compound according to claim 1 selected from:

1-methyl-4-[(4-chloro-2-thienyl)-(4-fluorophenyl)]methylene-piperidine and 1-methyl-4-[(4-methyl-2-thienyl)-(4-fluorophenyl)]methylene-piperidine;

or a pharmaceutically acceptable salt or solvate thereof.

6. A pharmaceutical formulation comprising a compound of formula (I) or a pharmaceutically acceptable salt or solvate thereof, as defined according to any of claims 1 to 5, together with a pharmaceutically acceptable carrier therefor.

7. A method of treating or preventing a psychotic disorder in an animal, comprising administering an effective amount of a compound of claim 1, or a pharmaceutically acceptable salt or solvate thereof, to the animal.

8. A process for the preparation of a formula (I) as defined in claim 1 comprising:

(A) reacting a compound of formula (II)

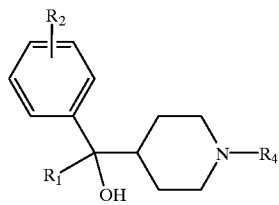
(II)

wherein $R_1$ and $R_2$ are as previously defined and $R_4$ is a group $R_3$ as defined in claim 1, with a dehydrating agent; or (B) simultaneously or sequentially dehydrating and deprotecting a compound of formula (II)

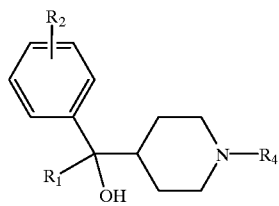
(II)

wherein $R_1$ and $R_2$ are as previously defined and $R_4$ is a nitrogen protecting group; or (C) reacting a compound of formula (III)

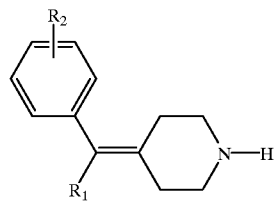
(III)

wherein $R_1$ and $R_2$ are as previously defined, with an alkylating agent; and thereafter, or simultaneously therewith, effecting one or more of the following optional conversions:
  (i) converting a pharmaceutically acceptable salt or solvate of a compound of formula (I) into a compound of formula (I),
  (ii) converting a pharmaceutically acceptable salt or solvate of a compound of formula (I) into another pharmaceutically acceptable salt or solvate of formula (I), and
  (iii) converting a compound of formula (I) into a pharmaceutically acceptable salt or solvate of a compound of formula (I).

9. A method of preparing a pharmaceutical formulation, comprising admixing an effective amount of a compound of claim 1, or a pharmaceutically acceptable salt or solvate thereof, with a pharmaceutically acceptable carrier.

* * * * *

UNITED STATES PATENT AND TRADEMARK OFFICE
CERTIFICATE OF CORRECTION

PATENT NO. : 6,288,085 B1
DATED : September 11, 2001
INVENTOR(S) : Rae et al.

It is certified that error appears in the above-identified patent and that said Letters Patent is hereby corrected as shown below:

<u>Claims 3 and 4,</u>
Line 1, insert -- , -- after "claim 1".

Signed and Sealed this

Twelfth Day of March, 2002

Attest:

*Attesting Officer*

JAMES E. ROGAN
*Director of the United States Patent and Trademark Office*